US006844328B2

United States Patent
Miglierini et al.

(10) Patent No.: US 6,844,328 B2
(45) Date of Patent: Jan. 18, 2005

(54) POLYSACCHARIDIC ESTERS OF N-DERIVATIVES OF GLUTAMIC ACID

(75) Inventors: Giuliana Miglierini, Varese (IT); Luca Stucchi, Pavia di Udine (IT); Alessandro Rastrelli, Padua (IT)

(73) Assignee: Eurand Pharmaceuticals Ltd. (IE)

( * ) Notice: Subject to any disclaimer, the term of this patent is extended or adjusted under 35 U.S.C. 154(b) by 0 days.

(21) Appl. No.: 10/221,703

(22) PCT Filed: Mar. 16, 2001

(86) PCT No.: PCT/EP01/03050

§ 371 (c)(1),
(2), (4) Date: Jan. 27, 2003

(87) PCT Pub. No.: WO01/68105

PCT Pub. Date: Sep. 20, 2001

(65) Prior Publication Data

US 2003/0158125 A1 Aug. 21, 2003

(30) Foreign Application Priority Data

Mar. 17, 2000 (IT) .................................. MI2000A0559

(51) Int. Cl.[7] ...................... A61K 31/715; A61K 31/70; C07H 13/02; C07H 1/00; C07H 11/00
(52) U.S. Cl. ............................ 514/54; 514/58; 514/69; 514/60; 514/62; 536/55.2; 536/55.3; 536/118; 536/119; 536/123; 536/123.12; 536/124
(58) Field of Search ..................... 514/54, 58, 59, 514/60, 62; 536/55.2, 55.3, 118, 119, 123.1, 124, 123.12

(56) References Cited

U.S. PATENT DOCUMENTS

| 4,851,521 A | 7/1989 | della Valle et al. ......... 536/55.1 |
| 5,554,386 A | 9/1996 | Groman et al. ............... 514/54 |
| 5,698,556 A | * 12/1997 | Chan ............................ 514/249 |
| 5,733,891 A | 3/1998 | Akima et al. .................. 514/59 |

FOREIGN PATENT DOCUMENTS

| CA | 2009695 | 8/1990 |
| DD | 267497 A1 * | 5/1989 |
| EP | 0383170 A2 * | 8/1990 |
| WO | 98/23648 | 6/1998 |
| WO | 99/02151 | 1/1999 |
| WO | 99/18133 | 4/1999 |

OTHER PUBLICATIONS

Levin, B., "Ulcerative Colitis and Colon Cancer: Biology and Surveillance," *Journal of Cellular Biochemistry*, Supplement 16G47–50 (1992).

Dechanet, J., et al., "IL–4 Inhibits Growth Factor–Stimulated Rheumatoid Synoviocyte Proliferation by Blocking the Early Phases of the Cell Cycle," *The Journal of Immunology*, vol. 151, No. 9, pp. 4908–4917 (Nov. 1, 1993).

Dang, Wenbin, "Covalent Coupling of Methotrexate to Dextran Enhances the Penetration of Cytotoxicity into a Tissue–like Matrix," *Cancer Research*, 54, pp. 1729–1735 (Apr. 1, 1994).

Goodman & Gilman's *The Pharmacological Basis of Therapeutics*, Ninth Edition, published by McGraw–Hill, pp. 1243–1244 (1996).

* cited by examiner

*Primary Examiner*—James O. Wilson
*Assistant Examiner*—Everett White
(74) *Attorney, Agent, or Firm*—Thompson Hine LLP

(57) ABSTRACT

The present invention is related to polysaccharide esters of N-derivatives of glutamic acid (N-GA derivatives). These polysaccharidic esters have antiproliferative activity and are characterized by a low systemic toxicity. The esters of the invention are used in the prevention and therapy of diseases caused by cellular hyperproliferation, particularly psoriasis, tumors, rheumatoid arthritis, or intestinal inflammatory pathologies.

26 Claims, No Drawings

POLYSACCHARIDIC ESTERS OF N-DERIVATIVES OF GLUTAMIC ACID

FIELD OF THE INVENTION

The present invention relates to new products, namely polysaccharidic esters of N-derivatives of glutamic acid (N-GA). Their use as antiproliferatives in pharmaceutics is herein described.

PRIOR ART

Several modified polysaccharides have been described in the art. They are obtained by chemical modification of some groups present on the polysaccharidic chain, such as for example the carboxylic groups, the amine groups, or the hydroxy groups with the formation of esters, amides, ethers. The application fields are several and include for example food, varnishes, analytical chemistry, cosmetics and pharmaceutics.

In the pharmaceutical area, polysaccharides are considered to be compounds suitable for the preparation of controlled drug-release compounds. They are in fact extremely well tolerated by the organism since, as for example hyaluronic acid and heparins, they are part of it.

The polysaccharides used for the controlled release of pharmacologically active molecules can be either present in a mixture with the drug (WO 99/02151) or covalently bound to it (U.S. Pat. Nos. 4,851,521 and 5,733,891) by means, for example, of either ester or amidic bonds.

Besides their function as carriers, however, some polysaccharides have their own biological activity or they are components of the organism: for example, heparins are anticoagulant agents; hyaluronic acid is the major component of the vitreous humour and synovial fluid and is moreover commonly used in clinical practice for the treatment of osteoarthrosis and arthropathies. Scleroglucan (Sizofiran®), another polysaccharide, is used in the treatment of tumours. Other sulphated polysaccharides turned out to be effective in the treatment of rheumatoid arthritis, retinitis and psoriasis.

The pharmaceutical use of N-derivatives of glutamic acid with inhibition activity of the dihydrofolate reductase enzyme (DHFR) is reported in the literature (Goodman & Gilman, The Pharmacological basis of Therapeutics, McGraw-Hill, 1996, pg. 1243). The enzyme DHFR is responsible for the recycling of 7,8-dihydrofolate to its reduced, physiologically active 6(R)-tetrahydro form. The availability of reduced folates is essential to support the replication of actively proliferating cells. The cytotoxic effect of N-derivatives of glutamic acid, which act as a potent inhibitors of DHFR, has been ascribed to the depletion of the intracellular pool of reduced folates. These drugs are commonly used as antiproliferatives in several kinds of pathologies such as neoplasms, psoriasis and rheumatoid arthritis. Their therapeutical use is however strongly limited by their high systemic toxicity, hence systems or more specific formulations allowing the administration of lower doses of the drug with a subsequent decrease of the toxicity are highly desirable.

Some of these N-GA derivatives have been linked to other molecules, in particular to macromolecules, such as serum albumine, or synthetic polymers, gelatine and some polysaccharides. For example, a poly-methotrexate-dextran has been prepared using a condensing agent (carbonylimidazole) (CA 2,009,695). This last reaction process does not allow the preparation of a structurally defined product because of the several different types of carboxylic and hydroxy groups, which react randomly. The structure of this product cannot be deeply elucidated, it is therefore only characterized by the amount of methotrexate present in the material isolated from the reaction mixture. In fact no evidence has been given about the position of substitution on polysaccharide. The same type of reaction process has been applied for the preparation of other polysaccharidic derivatives which again allow for the preparation of randomly substituted polymer (U.S. Pat. No. 5,554,386). Another attempt to introduce methotrexate on a polymer in order to prepare a pharmacological active system is a conjugation reaction between the polysaccharide dextran and the drug which occurs via a spacer group. Anyhow, prior to said conjugation the dextran is modified with periodate and its original saccharidic structure is thus destroyed leading to a different polymer (Dang et al., *Cancer Res.*, 54, 1729, 1994). Possible undesiderable cross-linking reaction between the carboxylic and the amino groups of the methotrexate are envisaged in some of the reactions used in the prior art.

SUMMARY

A class of polysaccharidic esters of the compounds of formula (I), commonly known as N-GA (N-derivatives of glutamic acid) represent the object of the present invention.

These N-GA compounds have the general formula:

formula (I)

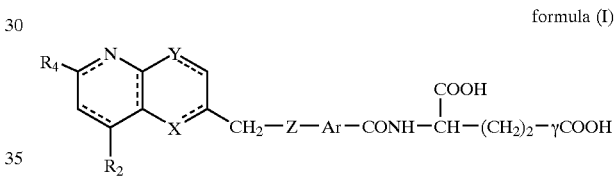

wherein:

$R_2$ and $R_4$ represent: —$NH_2$, —OH, —$OCH_3$, $C_1$–$C_5$ alkyl, =O and the 6-membered ring containing the two nitrogen atoms is optionally aromatic;

X and Y represent: —C($R_5$)=, —N= and the ring containing them is optionally aromatic, or they represent: —CH($R_5$)—, or —NH—, and the ring containing them is aliphatic, $R_5$ represents: —H, $C_1$–$C_5$ alkyl;

Z represents: —CH($R_{10}$)—, —N($R_{10}$)—, —O—;

$R_{10}$ represents: —H, $C_1$–$C_5$ alkyl, $C_1$–$C_5$ alkenyl, $C_1$–$C_5$ alkynyl, heterocyclic ring with 5–6 members with 1–3 heteroatoms selected in the group consisting of nitrogen, sulphur and oxygen;

Ar represents a 1,4-phenyl group possibly condensed with one or more 5–6 membered aromatic rings, possibly heterocycles and possibly substituted with $R_2$.

The polysaccharides used for the preparation of polysaccharidic esters are obtained from natural sources and their primary hydroxy groups present on the monosaccharidic units are totally or partially esterified with the γ-carboxylic group of the compounds of formula (I).

The products of the present invention can be used in the pharmaceutical area as inhibitors of the cell proliferation and are therefore useful in the preparation of medicaments for the treatment of neoplastic, inflammatory or autoimmune diseases.

The present invention further comprises new pharmaceutical compositions containing said polysaccharidic esters as active compounds in combination with suitable pharmaceutical excipients and/or solvents and their use in the treatment and the prevention of diseases characterised by cell hyperproliferation.

DETAILED DESCRIPTION OF THE INVENTION

The object of the present invention relates to a class of polysaccharidic esters of compounds of formula (I) commonly known as N-GA (N-derivatives of glutamic acid).

These N-GA compounds have the following general formula:

formula (I)

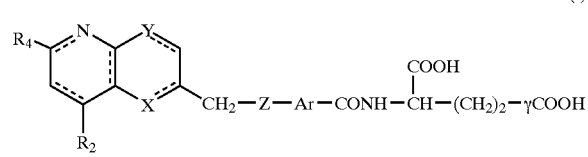

wherein:
$R_2$ and $R_4$ represent: —$NH_2$, —OH, —$OCH_3$, $C_1$–$C_5$ alkyl, =O and the 6-membered ring to which $R_2$ and $R_4$ are bound is optionally aromatic;

X and Y are selected in the group consisting of: —C($R_5$)=, —CH($R_5$)—, —NH—, —N=, wherein $R_5$ represents: —H, $C_1$–$C_5$ alkyl and the ring including X and Y is optionally aromatic;

$R_5$ represents: —H, $C_1$–$C_5$ alkyl;

Z represents: —CH($R_{10}$)—, —N($R_{10}$)—, —O—;

$R_{10}$ represents: —H, $C_1$–$C_5$ alkyl, $C_1$–$C_5$ alkenyl, $C_1$–$C_5$ alkynyl, 5–6 membered heterocyclic ring with 1–3 heteroatoms selected in the group consisting of nitrogen, sulphur and oxygen.

Ar represents: 1,4-phenyl optionally condensed with one or more 5–6 membered aromatic rings optionally heterocyclic and optionally substituted with $R_2$.

In formula (I), depending on whether the rings are aromatic or not, the following situations may occur:

1) when the 6-membered ring containing the two nitrogen atoms is aromatic, then both the nitrogen atoms are: —N= and the carbon atoms substituted by $R_2$ and $R_4$ are respectively: —C($R_2$)= and —C($R_4$)= and $R_2$ and $R_4$ are different from =O; moreover the carbon atoms linked to X and Y and common to both rings, are respectively: —C(X)= and —C(Y)=;

2) when the 6-membered ring containing the two nitrogen atoms is not aromatic, then both the nitrogen atoms are in the form: —NH—, and the carbon atoms substituted by $R_2$ and $R_4$ are respectively: —CH($R_2$)— and —CH($R_4$)— or when $R_2$ and/or $R_4$ are =O, the corresponding carbon atom is not substituted by H, and either: a) the carbon atoms linked to X and Y are: —CH(X)— and —CH(Y)—, when the ring containing X and Y is not aromatic; or b) they are —C(X)= and —C(Y)= when the ring containing X and Y is aromatic;

3) when the ring containing X and Y is aromatic then X and Y are: —C($R_5$)=, —N= and the carbon atoms linked to X and Y and common to both rings, are —C(X)= and —C(Y)= and the carbon atom linked to X and to —$CH_2$—Z— is not substituted by —H and the remaining carbon atom linked to Y is —CH=;

4) when the ring containing X and Y is not aromatic, then X and Y are —CH($R_5$)—, —NH— and either: a) the carbon atoms linked to X and Y (also belonging to the N-containing ring) are —C(X)= and —C(Y)= when said two N-containing ring is aromatic, or: b) they are —CH(X)= and —CH(Y)= when said N-containing ring is not aromatic, and the carbon atom linked to X and to —$CH_2$—Z— is substituted by —H and the remaining carbon atom which is linked to Y is —$CH_2$—.

In the polysaccharidic esters according to the invention, the primary hydroxy groups of the polysaccharide are partially or totally esterified with the γ-carboxylic group of the compounds of formula (I). The γ-carboxylic group of N-GA is the one directly linked to —$(CH_2)_2$—.

According to a first preferred embodiment of the invention, when $R_2$ and $R_4$ are —$NH_2$ or —OH, $R_5$ when present represents: —H, —$CH_3$, the 6-membered ring containing the two nitrogen atoms (—N=) is aromatic; Z is selected in the group consisting of: —CH($R_{10}$)—, —N($R_{10}$)—, wherein $R_{10}$ represents: —H, $C_1$–$C_5$ alkyl, $C_1$–$C_5$ alkenyl, $C_1$–$C_5$ alkynyl.

In a second preferred embodiment, when $R_2$ is =O and $R_4$ is —$NH_2$, the 6-membered ring containing the two nitrogen atoms is not aromatic; X and Y are nitrogen atoms (—N=) and the ring containing them is aromatic; Z is —N($R_{10}$)— wherein $R_{10}$ represents: —H or —$CH_3$; Ar is 1,4 phenyl.

In a third preferred embodiment, when $R_2$ and $R_4$ are —$NH_2$, the 6-membered ring containing the two nitrogen atoms (—N=) is aromatic; X and Y are nitrogen atoms (—N=), and the ring containing them is aromatic, moreover Z is —N($R_{10}$)—, wherein $R_{10}$ is —$CH_3$ or —H and Ar is 1,4 phenyl.

In a fourth preferred embodiment when $R_2$ and $R_4$ are —$NH_2$, the 6-membered ring containing the two nitrogen atoms (—N=) is aromatic; X and Y are nitrogen atoms (—N=) and the ring containing them is aromatic, Z is —CH($C_2H_5$)— and Ar is 1,4-phenyl. The esterification between the compounds of formula (I) and the polysaccharide takes place between the primary hydroxy groups of the monosaccharidic units of the polysaccharide and the γ-carboxylic groups of the compound of formula (I) (N-GA).

The degree of susbtitution of these polysaccharidic esters ranges from >0 to 1, preferably from 0.005 to 1. The term "degree of substitution" (DS) indicates the number of moles of formula (I) compounds (N-GA) per number of moles of monosaccharidic units containing a primary hydroxy group. A degree of substitution corresponding to 1 represents a product having all primary hydroxy groups esterified with N-GA.

The polysaccharides used in the present invention are either anionic or neutral and at least some of their monosaccharidic units contain primary hydroxy groups.

The polysaccharides are isolated from different sources: animals, humans, plants, microrganisms and their native weight average molecular weight (MW) ranges from $1 \times 10^3$ to $2 \times 10^6$.

The polysaccharides have either a linear or branched structure and are composed of monosaccharidic units such as: D-glucose, D-xylose, D-arabinose, D- and L-mannose, D-galactose, L-fucose, D-fructose, L-rhamnose, D-glucuronic acid, D-mannuronic acid, L-guluronic acid, L-iduronic acid, D-galacturonic acid, N-acetyl-D-glucosamine, N-acetyl-D-galactosamine, 3,6-anhydro-D-galactose, N-acetyl-D-galactosamine, 3,6-anhydro-D-galactose, 3,6-anhydro-L-galactose. These monosaccharides may optionally contain sulphate or acetyl groups.

The main polysaccharidic chain has a β-(1→3)- or β-(1→2) or β-(1→4)-D-glycosidic or α-(1→3)-, α-(1→4)-α-(1→6)-glycosidic structure; the β-configuration is the preferred one. The side chains are preferably composed of D-glycosyl units bound with a β-(1→2), β-(1→3), β-(1→4), β-(1→6), or α-(1→4), α-(1→, 6) or even more preferably β-(1→6) bonds.

When the polysaccharide is neutral, it is preferably a glucan (a glucose polysaccharide) isolated from algae, fungii, plants, bacteria or yeasts. Preferred neutral polysaccharides belong to the class of β-(1→3)-D-glucans (polysaccharide of β-(1→3)-D-glucose) and are either linear or branched. Preferred examples of glucans that can be used in the present invention are: scleroglucan, lentinan, schizophyllan, pachimaran, curdlan, laminaran, pullulan. Said polysaccharides are produced in large amounts by algae, yeast and fungi. Among them scleroglucan is the preferred one. Scleroglucan is a β-(1→3)-D-glucan with a side chain constituted by a β-(1→6)-D-glucose unit at every third glucose in the main chain. This polysaccharide is mainly extracted from fungi, such as *Sclerotium glucanicum* or *S. rolfsii*. Fungal fermentation represents a further useful way of their production.

When the polysaccharide is anionic, carboxylated polysaccharides, such as hyaluronic acid or its salts (dimeric unit composed of N-acetyl-D-glucosamine and D-glucuronic acid) are used. Pectin is another example of anionic polysaccharide. Pectin is a polysaccharide composed of D-galacturonic acid and D-galactose, where carboxylic groups can be partially esterified with methyl groups. Another class of anionic polysaccharides used in the esters of the present invention, are represented by sulphated polysaccharides, such as for example heparins, chondroitin sulphate or dermatan sulphate. Other examples of sulphated polysaccharides useful for the preparation of the esters of the present invention, are isolated from algae of the *Grateloupia doryphora* or *G. filicina* species as described in WO 98/23648. Other sulphated polysaccharides isolated from different algae belonging to the *Grateloupiaceae* or the *Codiaceae* families or from other microorganisms can also be profitably used.

In case of the anionic polysaccharides, the esters of the present invention are optionally salified with alkaline metals (preferably Na and K), earth-alkaline metals (preferably Ca and Mg), transition metals (preferably Cu, Zn, Ag, Au, Co). Derivatized polysaccharides such as the one obtained by salification of the compound of the present invention, are obtained by processes known by the skilled artisan.

Optionally, the possible free hydroxy groups on the monosaccharidic unit of the polysaccharidic esters of the invention, are further modified by the introduction of one or more substituents selected in the group consisting of: lower $C_1$–$C_6$ alkyls, —COOH, $NH_2$, —NH—$COCH_3$, —$SO_3H$, —$OPO_3H_2$, —COO—$(CH_2)_n$—COOH, —COOR, —COR, —OR, —O—$(CH_2)_n$—OCOR, wherein n=1–4 and R=$C_1$–$C_{10}$ alkyl. These substitutions can be easily obtained by processes known in the art, and chosen for example to modify the hydrophilic character of the polysaccharidic esters modulating their solubility.

The polysaccharidic esters of the present invention have peculiar chemical features consisting both in the presence of a double regioselectivity and in the maintenance of the native polysaccharidic structure. Furthermore, no spacer arm or chemical group is present between the N-GA and the polysaccharide.

As far as the double regioselectivity is concerned, the term "double" refers to both selectivity on the polysaccharide and on the N-GA. The resulting derivative is therefore unique. In fact, among the several hydroxy groups present on the polysaccharide only the primary hydroxy groups of the monosaccharidic units are esterified with N-GA. About the selectivity on N-GA, although this molecule contains two reactive carboxylic groups which show quite similar chemical reactivity, the derivatives of the present invention concern the products having only one specific carboxylic acid involved in the reaction and more precisely the γ-carboxylic acid, as confirmed for example by NMR spectroscopy. As a consequence, the derivatives of the invention have a tridimensional structure which is highly regular and defined. This feature provides a definite pharmacological advantage over the randomly substituted derivatives of the prior art. As a matter of fact the random substitution of the possible free either primary or secondary hydroxy groups lead to products with a variable activity dependent on the substitution pattern.

Furthermore, differently from the macromolecular derivatives of N-GA of the prior art, in the esters of the present invention the polysaccharide maintain the original native chemical structure. The starting polysaccharide is herein modified in the sense that new groups are introduced on the monosaccharidic units but the structural identity of the monosaccharidic unit is not modified. The integrity of polysaccharides is hence preserved with the advantage that only known biocompatible metabolites are produced (native polysaccharide such as glucan or hyaluronan) after the in vivo hydrolysis of the ester linkage. According to a further embodiment, the present invention is related to the process for the preparation of the polysaccharidic esters of N-GA.

The esterification process of the compounds of formula (I) with the polysaccharides occurs by regioselective reaction of the activated primary hydroxy groups of the monosaccharidic units of the polysaccharide with the γ-carboxyl group of N-GA. By choosing the appropriate amounts of reactants, polysaccharidic esters with different degree of substitution are obtained. The process comprises the following steps:

a) activation of the primary hydroxy groups of the monosaccharidic units of the polysaccharide by halogenation with the obtainment of regioselective halogenated polysaccharide;

b) formation of ester linkage between the halogenated polysaccharide of step a) and the carboxyl groups of the N-GA by displacement of the halogen atoms.

Step a) is performed by suspending the polysaccharide in a suitable organic solvent under stirring for 1–5 hours at 25–100° C., followed by the activation of the primary hydroxy groups which is carried out in the presence of an alkyl or aryl halide in an organic solvent at temperature comprised between −20° C. and 70° C. under stirring for 1–18 hours; suitable halides are methanesulphonylbromide, p-toluenesulphonylbromide, methanesulphonylchloride, p-toluenesulphonylchloride; suitable solvents are dimethylformamide, dimethylsulphoxide, N-methylpyrrolidone. This reaction mixture can be optionally alkalinised up to a pH value between 9 and 11. At the end of the halogenation the mixture is neutralised and the halogenated polysaccharide is recovered by means of known techniques such as precipitation, drying, freeze-drying. When the polysaccharide is an anionic one it can be used either in the free or in the salified form, preferably in the salified form.

Step b) is carried out by suspending in organic solvent or mixture thereof the halogenated polysaccharide obtained in a), followed by addition of N-GA in the same organic aprotic solvent of mixture thereof, in the presence of a basic agent. The reaction is carried out at room temperature, under stirring for 0.5–3 days. Suitable solvents are dimethylformamide, dimethylsulphoxide, N-methylpyrrolidone. At the end of the reaction the polysaccharidic ester of N-derivatives of glutamic acid is recovered by means of known techniques such as precipitation, drying, freeze-drying.

Further details about the halogenation of the polysaccharide (step a) of the process of the present invention are found in WO 99/18133, the conditions described herein can be applied to both anionic and neutral polysaccharides.

Other esterification reactions of the polysaccharide with the compounds of formula (I) which allow the double regioselectivity, such as reactions comprising protection and deprotection of the specific chemical groups on which the selective derivatisation occurs can be applied as well.

The esters of the present invention inhibit cell hyperproliferation and have a surprisingly low systemic toxicity.

In particular, the products of the invention are active in the treatment of all those pathologies and disorders characterized by cell hyperproliferation such as inflammatory, autoimmune or neoplastic diseases and in particular in inflammatory pathologies which are susceptible of neoplastic degeneration, such as intestinal inflammatory diseases, i.e. diverticulitis, Crohn's disease, inflammation of the colon, ulcerative colitis, as described in Levin et al. (J. Cell. Biochem. Suppl., 1992, 16G:47–50). The polysaccharidic esters of the present invention are used also in the treatment of synovial cell proliferation, which leads to degeneration of the articular cartilage, of the bone or the tendons, as described in Echanet et al. (J. Immunol., 1993, 151(9) 4908–4917). Such degeneration is frequent in articular diseases such as for example rheumatoid arthritis, juvenile arthritis, psoriatic arthritis. The compounds according to the invention are used also in dermatological disorders characterised by abnormal cells proliferation and even in the control of secondary cell proliferation for example in the surgical insertion of prosthetic medical devices (for example cardiovascular stents, or others aids) or vascular disorders or in asthmatic attacks, myocardial infarct or pulmonary hypertension.

As far as antineoplastic disease are concerned the product of the invention can be useful applied for the treatment of several type of human tumors, such as for example ovarian carcinoma, lymphoblastic leukemia, lymphoma, choriocarcinoma, breast cancer, squamous cell carcinoma, osteosarcoma.

In a further embodiment, the present invention provides for pharmaceutical compositions containing the ester derivatives of the invention in combination with pharmaceutical suitable excipients and/or diluents. Said compositions the polysaccharidic esters of the invention may optionally comprise other known drugs with antiproliferative activity.

The pharmaceutical compositions according to the present invention are suitable for parenteral, oral or topical administration. The preferred parenteral modes of administration are intravenous, intramuscular, intrarticular, subcutaneous. When they are in liquid form, the compositions can be in the form of a solution or suspension, both in aqueous or non-aqueous medium. Alternatively, the compositions can be formulated in a solid form wherein the lyophilized or dried product is dissolved or suspended by the addition of a suitable liquid medium immediately prior to administration. The pharmaceutical compositions in a solid or semi-solid form are insertions, gels, cream, granules, powders, tablets, capsules, pills or microencapsulated formulations. Other types of preparation can be set up by techniques known to the expert.

The doses of the ester derivatives according to the invention can vary depending on the kind and seriousness of the pathology and depend on the age, weight and general conditions of the patient.

EXPERIMENTAL PART

EXAMPLE 1

Methods of Determination of Weight Average Molecular Weight (Mw)

The molecular weight of the polysaccharidic reagents) was analysed by HP-SEC (High Performance Size Exclusion Chromatography). The analysis conditions were:

Cromatograph: HPLC Jasco PU-980 with Rheodyne 9125 injector. Column: TSK Pwxl G6000+G5000+G3000 (TosoHaas) 300 mm×7.8 mm ID, 13, 10, 6 μm particle size; Temperature 40° C.

Mobile phase: NaCl 0.15 M.

Flux: 0.8 ml/min.

Detector. LALLS CMX-100 (TSP Chromatix), Po=150 mV; Differential Refractive Index 410 (Waters), Sensitivity 128x; Temperature 32° C.

Injected volume: 100 μl

The samples to be analysed were solubilised in 0.15 M NaCl at the concentration of ca. 1.0 mg/ml and kept under stirring for 12 hours. Then, the solutions were filtered on a 0.45 μm porosity filter (Millipore) and finally injected in the chromatograph. The analysis allow the measurement of Mw (weight average molecular weight), Mn (number average molecular weight), PI (polydispersity). The concentration of the polymeric samples solutions were controlled by means of the integral of the refractive index.

EXAMPLE 2

Preparation of Halogenated Scleroglucan 160 mL of anhydrous DMF was heated at 80° C. and mixed for 1 hour under nitrogen. 1 g of scleroglucan having weight average molecular weight of 60000 (determined as described in ex. 1), was added and the system was mixed for three hours. The solution was cooled to room temperature. 9.8 g of methanesulphonylbromide was then added at 0° C. to the solution. The reaction mixture was kept under mixing for another 20 minutes and then heated at 80° C. for 16 hours. The mixture was cooled to room temperature and the reaction as stopped by the addition of 30 mL of Milli-Q water. The mixture was neutralized with 3N NaOH, then concentrated under reduced pressure and finally poured into 800 mL of acetone. The product was collected by filtration, washed with acetone, suspended in distilled water and dialysed. The mixture was filtered and the solid material was dried in oven under vacuum at room temperature. Weight of the solid: 1 g.

The product was analysed with $^{13}$C NMR spectroscopy (DEPT) in DMSO-$d_6$/TFA a 50° C. The signal of $CH_2$—O (C6) of the polysaccharide which is involved in halogenation is present at 34.5 ppm, whereas the same group in the underivatised polysaccharide gives a signal at 61 ppm. The change in chemical shift provides the proof that the halogenation reaction took place on the primary hydroxy groups of the glucose residues.

EXAMPLE 3

Esterification of Scleroglucan with the Compound MT

The compound MT of formula (I) carrying the following substituents: $R_2$ and $R_4$; —$NH_2$, the 6-membered ring containing the two nitrogen atoms was aromatic; X and Y are —N= and the ring that contains them was aromatic; Z was —N(CH$_3$)—; Ar was 1,4-phenyl, was esterified with the halogenated scleroglucan.

150 mg of halogenated scleroglucan, as obtained in example 2 was dissolved in 15 mL of DMSO at 80° C. After 3 hours the solution was cooled to room temperature and 512 mg of MT in 10 mL DMSO was added. The reaction mixture was kept at room temperature under mixing, in the presence of a basic agent, under nitrogen and protected from light for 48 hours. Then the product was precipitated in 250 mL of acetone and collected by filtration, washed with acetone, suspended in distilled water and neutralized with 0.2 N HCl, and again precipitated with acetone. The solid was dried in oven under vacuum at room temperature. Weight of the solid: 80 mg.

Analysis of the product: FT-IR spectroscopy (Perkin-Elmer mod. 1750): band at 1730 cm$^{-1}$ (KBr pellet) typical of ester linkage. $^1$H NMR spectroscopy (NMR Varian Inova 500—500 MHz): diffusion experiments on product dissolved in DMSO-d$_6$/TFA at 23° C. showed the presence of MT covalently bound to the polysaccharide. The product was analysed with $^1$H NMR spectroscopy in DMSO-d$_6$/TFA at 50° C. From the analysis of the spectrum it is evident the modification of the signals due to the γ-methylene group of MT: the protons are not equivalent and they split into two multiplets (2.35 e 2.45 ppm) whereas the corresponding group of the starting MT (that is the MT not bonded to the polysaccharide) was characterised by a signal in the form of a triplet. The non equivalence of the γ-protons, due to the esterification of the carboxylic acid, is confirmed in the heterobinuclear spectrum $^1$H—$^{13}$C HSQC ($^{13}$C signal at 32 ppm).

EXAMPLE 4

Preparation of Halogenated Scleroglucan 300 mg of scleroglucan with weight average molecular weight of 995000 (determined as described in example 1) was suspended in 40 mL of anhydrous DMF at 80° C. and kept under mixing and under nitrogen atmosphere for 1 hour. The mixture was cooled to room temperature and then 2.9 g of methanesulphonylbromide was added at 0° C. The reaction mixture was kept under mixing for another 30 minutes and then heated at 80° C. for 16 hours. The mixture was cooled to room temperature and the reaction was stopped by the addition of 8 mL of Milli-Q water. The mixture was neutralized with 0.1 N NaOH, concentrated under reduced pressure and poured in 200 mL of acetone. The product was collected by filtration, washed with acetone, suspended in distilled water, and then dialysed against distilled water and then freeze-dried Weight of the solid: 290 mg.

The product was analysed with $^{13}$C NMR spectroscopy which showed that the halogenation reaction occurred on the primary hydroxy groups as described in example 2.

EXAMPLE 5

Esterification of Scleroglucan with MT 90 mg of halogenated scleroglucan as obtained in example 4, was suspended in 20 mL of DMSO at 80° C. After 4 hours the mixture was cooled to room temperature and 293 mg of MT dissolved in 20 ml DMSO was added. The reaction mixture was kept to room temperature, in the presence of a basic agent, under mixing, under nitrogen and protected from light for 48 hours. Then the mixture was poured in 250 mL of acetone. The product was collected by filtration, extensively washed with MeOH, filtered and finally dried in oven under vacuum at room temperature. Weight of the solid: 90 mg.

The product was analysed with $^1$H NMR spectroscopy in DMSO-d$_6$/TFA, which showed the presence of MT covalently bound to the polysaccharide as described in example 3.

EXAMPLE 6

Preparation of Halogenated Scleroglucan 600 mg of scleroglucan with weight average molecular weight of 140000 (determined as described in ex. 1) was suspended in 40 mL of anhydrous DMF at 80° C., under mixing and under nitrogen for 1 hour. The mixture was cooled to room temperature and then 5.9 g of methanesulphonylbromide was added at 0° C. The reaction mixture was kept under mixing for 30 minutes and then heated at 80° C. for 16 hours. The mixture was cooled to room temperature and the reaction was stopped by the addition of 8 mL of Milli-Q water. The mixture was neutralized with 0.1 N NaOH, concentrated under reduced pressure and precipitated in 200 mL of acetone. The product was collected by filtration, washed with acetone, suspended in distilled water, and then dialysed against distilled water and then freeze-dried. Weight: 710 mg.

The product was analysed with $^{13}$C NMR spectroscopy which showed that halogenation reaction occurred on the primary hydroxy groups as observed in the compounds described in example 2.

EXAMPLE 7

Esterification of Scleroglucan with MT 500 mg of halogenated scleroglucan obtained in example 6 were suspended in 110 mL of DMSO at 80° C. After 4 hours the mixture was cooled to room temperature and 1,63 g of MT in 33 mL of DMSO was added. The reaction mixture was kept to room temperature, in the presence of a basic agent, under mixing, under nitrogen with exclusion of light for 48 hours. Then the product was precipitated in 250 mL of acetone and collected by filtration, washed with acetone, suspended in distilled water and neutralized with 0.2N HCl, and again precipitated with acetone. Weight of the product (RG4900): 470 mg.

The product was analysed with $^1$H NMR spectroscopy in DMSO-d$_6$/TFA, which showed the presence of MT covalently bound to the polysaccharide as described in example 3.

EXAMPLE 8

Preparation of Halogenated Hyaluronan 1 g of tetrabutylammonium salt of hyaluronic acid with weight average molecular weight of 120000 (determined as described in ex. 1) was suspended in 50 mL of anhydrous DMF at 80° C. and kept under mixing and under nitrogen atmosphere for ca 1 hour. The mixture was cooled down to room temperature and then 1.28 g of methanesulphonylbromide was added at 0° C. The reaction mixture was kept under mixing for another 30 minutes and then heated at 80° C. for 16 hours. The mixture was cooled down to room temperature and the reaction was stopped by the addition of ca 10 mL of Milli-Q water. The mixture was neutralized with 0.1 N NaOH, concentrated under reduced pressure and poured in 200 mL of acetone. The product was collected by filtration, washed with acetone, suspended in distilled water, and then dialysed against distilled water and freeze-dried Weight of the solid: 480 mg.

The product was analysed with $^{13}C$ NMR spectroscopy (DEPT) in DMSO-$d_6$/TFA a 50° C. The signal of $CH_2$—O (C6) of the polysaccharide involved in halogenation is present at 34.5 ppm, whereas the same group in the underivatised polysaccharide gives a signal at 61 ppm. The change in chemical shift provides the proof that the halogenation reaction took place on the primary hydroxy groups of the glucose residues.

EXAMPLE 9

Esterification of Hyaluronan with MT 50 mg of halogenated hyaluronan as obtained in example 8, was suspended in 5 mL of DMSO at 80° C. After 2–3 hours the mixture was cooled down to room temperature and 59 mg of MT dissolved in 2 ml DMSO was added. The reaction mixture was kept to room temperature, in the presence of a basic agent, under mixing, under nitrogen atmosphere and protected from light for 48 hours. Then the mixture was poured in 50 mL of acetone. The product was collected by filtration, thoroughly washed with MeOH, filtered and finally dried in oven under vacuum at room temperature. Weight of the solid: 70 mg.

The product was analysed with $^1H$ NMR spectroscopy in DMSO-$d_6$/TFA, showing the presence of MT covalently bound to the polysaccharide.

EXAMPLE 10

Effect of the Compound of the Invention on the Activity of Dihydrofolate Reductase Reagents and test samples were added to 3 ml disposable cuvettes to the required volume of distilled water in the following order: $H_2O$ (0.1–0 ml), 1.5 M Na-acetate buffer (1 ml), 1.8 M KCl (1 ml), 3 mM NADPH (0.15 ml), test solution in PBS (0–0.1 ml), dihydrofolate reductase (DHFR) (ca. 0.01 U/$\mu$l) (5 $\mu$l). All reagents were purchased from Sigma. The DHFR was introduced, mixed and incubated at 30° C. for 2 min. The reaction was initiated by the addition of dihydrofolic acid (3 mM, 0.15 ml), and the decrease in absorbance with the time at 340 nm was followed. The test solutions contained: a) MT (defined in example 3), $2.2 \times 10^{-5}$ M, b) the compound of the invention as obtained in example 7(RG4900) in amount corresponding to $2 \times 10^{-5}$ M MT equivalents.

A control reaction, which contained 0.1 ml of PBS as test solution was included.

The tested concentration of MT of $2.2 \times 10^{-5}$ M completely inhibited the activity of dihydrofolate dehydrogenase. The equimolar concentration, as referred to MT, of compound RG4900, did not inhibit the DHFR activity, as proved by a $\Delta A_{340}$ equal to the control reaction. However at the beginning of the reaction the rate of absorbance decrease is slightly lower in the presence of the compound then in the control. This observed residual inhibitory action of compound RG4900 on DHFR might be possibly ascribed to low amount of free MT present in the preparation. In conclusion, most of the DHFR inhibitory activity of is performed by MT, once released from the pro-drug after hydrolysis of the ester linkage in the appropriate cell compartment.

The conditions of esters hydrolysis have been studied by performing several experiments at different pH. The test of DHFR inhibition performed after the hydrolysis allowed to evidentiate the inhibiting activity of the hydrolised system.

EXAMPLE 11

In vitro Assay of the Antiproliferative Activity of the Compounds of the Invention The antiproliferative activity of the polysaccharidic ester of compound RG4900 of the invention was tested on several tumor cell lines, such as: SK-OV-3 (human cell line): ovarian carcinoma cells, HT29 colon carcinoma cells (human cell line), NIH-H460 pulmonary carcinoma cells (human cell line), L1210 leukemya cells (murine cell line). The above cell lines were grown as monolayer in RPMI-1640 medium (Sigma Chemical Co., St. Louis) supplemented with 10% FCS, at a physiological folate concentration (2 nM), in a 50 $cm^2$ plastic bottle (Corning Industries, Corning, N.Y.) kept at the temperature of 37° C., under damp atmosphere containing 5% of $CO_2$. They were passaged weekly into fresh medium. Before the beginning of the experimental tests, the cells in the exponential growth phase were removed from the flasks with a solution of trypsin. The cells were then seeded in 6-wells trays (30.000 cells/dish) in RPMI-1640 medium supplemented with 10% FCS. The cells were grown for 24 hours, in order to promote the adhesion, and the medium was then removed and replaced with the experimental medium. The cells were incubated for 72 or 120 hours. The experimental medium was prepared by diluting a stock solution in PBS buffer of the polysaccharidic ester of the invention at different final concentrations in a range of concentration comprised between 0–5000 $\mu$g/ml N-GA equivalent), in RPMI-1640 medium supplemented with 10% FCS. A comparative test was carried out with the corresponding N-GA in the concentration range 0–100 $\mu$g/ml. The antiproliferative activity was determined by means of the trypan blue colorimetric assay, which is proportional to the number of viable cells.

Table 1 shows the growth percentage of the cell line SK-OV-3 (ovary carcinoma), in the presence of the compound of example 7 (RG4900) after 72 and 120 hours of treatment. Each value is the average of 4 different tests. The concentrations of the compounds tested are referred to the amount of the MT present in the corresponding compound. The experiments were carried out with a cell density equal to 30.000 cells/dish.

TABLE 1

| Compound | Concentration (ng/ml) | % survival (72 h) | % survival (120 h) |
| --- | --- | --- | --- |
| RG4900 | 0 | 100 | 100.0 |
| " | 2.28 | n.d. | 106.5 |
| " | 6.58 | 83 | 76.0 |
| " | 20.5 | 84.5 | 45.0 |
| " | 60 | 55 | 13.0 |
| " | 185 | 46.5 | 5.5 |
| " | 550 | 38.5 | 3.0 |
| " | 1670 | 38.5 | 2.0 |
| " | 5000 | 32.5 | 1.0 |

From the data shown above, it is evident that the polysaccharidic esters according to the present invention exert a high antiproliferative activity, which is time- and dose-dependent.

Table 2 reports the effect on cell survival of SK-OV-3 ovary carcinoma both of the polysaccharidic ester and of the corresponding underivatised polysaccharide (scleroglucan, SC with MW: 140000). Tests were carried out after 72 and 120 hours of incubation and at a concentration of polysaccharidic ester corresponding to a 5 μg/ml concentration of MT.

TABLE 2

| Compound | | Concentration (μg/ml) | % survival |
|---|---|---|---|
| RG4900 | (72 h) | 0.34 | 32.5 |
| " | (120 h) | 0.34 | 1.0 |
| SC | (72 h) | 0.34 | 95 |
| SC | (120 h) | 0.34 | 99 |

From the data above no effect due to the underivatised polymer (SC) is to be acknowledged.

Table 3 shows the values of $IC_{50}$ (concentration necessary to reduce cell growth to 50% of the growth of the control) of the polysaccharidic esters of the invention and of a compound (AB1) prepared by derivatization of scleroglucan according to the prior art.

Counting of cell samples of the different tumor cell lines were carried out after 120 hours of treatment. The concentrations of the esters of the invention are expressed as the quantity of MT present on the polysaccharidic ester (ng/ml)

TABLE 3

| Cell line | Compound RG4900 (ng/ml) | Compound AB1 (ng/ml) |
|---|---|---|
| SK-OV-3 | 18 | 800 |
| L1210 | 24 | 820 |
| HT29 | 20 | 410 |
| NIH-H460 | 430 | Nd |

The data showing table 3 demonstrate that a randomly substituted MT-scleroglucan (AB1) prepared accordingly to example 3 of U.S. Pat. No. 5,554,386 and tested as a comparison, presents very high $IC_{50}$ with respect to the compounds of the invention. This provides the clear indication that a strong positive effect on the anti-proliferative activity of the compounds of the invention is obtained by selective substitution of N-GA.

What is claimed is:

1. A polysaceharidic ester of the compound of formula (I)

formula (I)

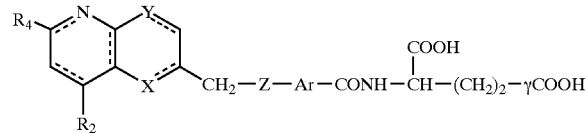

wherein:
R$_2$ and R$_4$ are independent from one another, are selected from the group consisting of —NH$_2$—, —OH, —OCH$_3$, C$_1$–C$_5$ alkyl, and =O, and the 6-membered ring containing the two nitrogen atoms is optionally aromatic;

X and Y are selected from the group consisting of —C(R$_5$)=, —CH(R$_5$)—, —NH—, and —N=, and wherein R$_5$ represents —H or C$_1$–C$_5$ alkyl, and the ring including X and Y is optionally aromatic;

Z is selected from the group consisting of —O—, —CH(R$_{10}$)—, and —N(R10)—, and wherein R$_{10}$ represents —H, C$_1$–C$_5$ alkyl, C$_1$–C$_5$ alkenyl, C$_1$–C$_5$ alkynyl, or a 5–6 membered heterocyclic ring with 1–3 heteroatoms selected from the group consisting of nitrogen, sulphur and oxygen;

Ar is 1,4-phenyl, possibly condensed with one or more 5–6-membered aromatic rings, optionally heterocycles, optionally substituted with R$_2$ as defined above; characterized in that only the primary hydroxy groups present on the monosaccharide units of the polysaccharide are either partially or totally esterified with the γ-carboxylic group of the compounds of formula (I).

2. A polysaceharidic ester according to claim 1 wherein:
R$_2$ and R$_4$ are independent from one another, are selected from the group consisting of —NH$_2$ and —OH, and the 6-membered ring containing the two nitrogen atoms is aromatic;
R$_5$, if present, represents —H, —CH$_3$;
Z is selected from the group consisting of —CH(R$_{10}$)— and —N(R$_{10}$)—, and wherein R$_{10}$ represents —H, C$_1$–C$_5$ alkyl, C$_1$–C$_5$ alkenyl, or C$_1$–C$_5$ alkynyl.

3. A polysaceharidic ester according to claim 1 wherein:
R$_2$ and R$_4$ are independent from one another, are selected from the group consisting of —NH2 and =O, and the 6-membered ring containing the two nitrogen atoms is not aromatic;
R$_5$, if present, represents —H or —CH3;
Z is selected from the group consisting of —CH(R$_{10}$)— and —N(R$_{10}$)—, and wherein R$_{10}$ represents —H, C$_1$–C$_5$ alkyl, C$_1$–C$_5$ alkenyl, or C$_1$–C$_5$ alkynyl.

4. A polysaceharidic ester according to claim 1 wherein:
R$_2$ is =O, R$_4$ is —NH$_2$ and the 6-membered ring containing the two nitrogen atoms is not aromatic;
X and Y are —N= and the ring containing them is aromatic;
Z is —N(R$_{10}$)— wherein R$_{10}$ represents —H or —GH$_3$; and
Ar is 1,4 phenyl.

5. A polysaceharidic ester according to claim 1 wherein:
R$_2$ and R$_4$ are —NM2 and the 6-membered ring containing the two nitrogen atoms is aromatic;
X and Y are —N=and the ring containing them is aromatic;
Z is —N(R$_{10}$)—, wherein R$_{10}$ is —CH3 or —H; and —Ar is 1,4-phenyl.

6. A polysaceharidic ester according to claim 1 wherein:
R$_2$ and R$_4$ are —NH$_2$ and the 6-membered ring containing the two nitrogen atoms is aromatic; —X and Y are —N=and the ring containing them is aromatic,
Z is —CH(C$_2$H5)—; and
Ar is 1,4 phenyl.

7. A polysaceharidic ester according to claim 1, wherein the polysaccharide is neutral or anionic.

8. A polysaceharidic ester according to claim 7, wherein the polysaccharide is either linear or branched and is composed of the monosaceharidic units selected from the group consisting of D-glucose, D-xylose, L-rhamnose, D-galacturonic acid, D-glucuronic acid, D-mannuronic acid, L-guluronic acid, L-iduronic acid, D-fructose, N-acetyl-D-glucosamine, N-acetyl-L-galactosamine, 3,6-anhydro-D-galactose, and 3,6-anhydro-L-galactose.

9. A polysaceharidic ester according to claim 8, wherein the main chain of said polysaccharide has β-(1→3), β-(1→2), β-(1→4)-D-glycosidic structure or α-(1→3), α-(1→4), α-(1→6)-glycosidic structure and the possible side chains are composed of monosaccharides bound with the configuration β-(1→2), β-(1→3), β-(1→4), β-(1→6), α(1→4), or α-(1→6).

10. A polysaceharidic ester according to claim 9, wherein said polysaceharide is a β-(→3)-D-glucan.

11. A polysaccharidic ester according to claim 10, wherein said polysaccharide is selected in the group consisting of: scleroglucan, lentinan, schizophyllan, pachimaran, curdlan, laminaran.

12. A polysaccharidic ester according to claim 9, wherein said polysaccharide is hyaluronic acid or its salts.

13. A polysaccharidic ester according to claim 9, wherein said polysaccharide is a sulphated polysaccharide.

14. A polysaccharidic ester according to claim 1, wherein at least one hydroxy group of the monosaccharidic units of the polysaccharide is substituted with a residue selected in the group consisting of: $C_1$–$C_6$alkyl, —COOH, —$NH_2$, —$NHCOCH_3$, —$SO_3H$, —$OPO_3H_2$, —COO—$(CH_2)_n$—COOH, —COOR, —COR, —OR, —O—$(CH_2)_n$OCOR and wherein n=1–4 and R= $C_1$–$C_{10}$ alkyl.

15. A pharmaceutical composition comprising as an active compound the polysaccharidic esters according to claim 1, in combination with suitable pharmacologically acceptable excipients and/or diluents.

16. A pharmaceutical composition according to claim 15 in the form of a solution or a suspension.

17. A pharmaceutical composition according to claim 15 in the form of a gel, cream, powder, granular powder, tablet, pill, capsule or insert.

18. A method for the treatment of rheumatoid arthritis comprising administering to a patient in need thereof the polysaccharidic ester according to claim 1.

19. A method for the treatment of psoriasis comprising by administering to a patient in need thereof the polysaccharidic ester according to claim 1.

20. A method for the treatment of tumors comprising administering to a patient in need thereof the polysaccharidic ester according to claim 1.

21. A process for the preparation of the polysaccharidic ester of claim 1 comprising the following steps:

a) obtainment of a regioselective halogenated polysaccharide by activation of the primary hydroxy groups of the monosaccharidic units of the polysaccharide; and b) formation of an ester bond between the regioselective halogenated polysaccharide and the carboxyl group of compound of formula (I) by displacement of the halogen atoms.

22. A process according to claim 21 wherein said activation in step a) is performed by halogenation of the polysaccharide.

23. A process according to claim 22 wherein said halogenation is performed in an organic solvent further comprising an alkyl- or aryl-halide.

24. A process according to claim 23 wherein said alkyl- or aryl-halide is chosen from the group consisting of methanesulphonylbromide p-toluenesulphonylbromide, methanesulphonylchloride, and p-toluenesulphonylcloride.

25. A process according to claim 21 wherein in step b) the halogenated polysaccharide obtained in step a) is suspended in an organic solvent and then mixed with the compound of formula (I), and suspended in the same organic solvent, in the presence of a basic agent.

26. A process according to claim 25 wherein said organic solvent is chosen from the group consisting of dimethylformamide dimethylsuiphoxide, and N-methylpyrrolidone.

* * * * *

UNITED STATES PATENT AND TRADEMARK OFFICE
CERTIFICATE OF CORRECTION

PATENT NO. : 6,844,328 B2
DATED : January 18, 2005
INVENTOR(S) : Giuliana Miglierini et al.

It is certified that error appears in the above-identified patent and that said Letters Patent is hereby corrected as shown below:

Column 13,
Line 42, change "polysaceharidic" to -- polysaccharidic --.
Line 54, change "-NH$_2$-" to -- -NH$_2,$ --.
Line 63, change "(R10) second occurrence to -- (R$_{10}$) --.

Column 14,
Line 3, after "above," begin a new paragraph.
Lines 8, 17, 27, 35, 51, 59, 66 and 67, change "polysaceharidic" to
-- polysaccharidic --.
Line 32, change "-GH$_3$" to -- -CH$_3$ --.
Line 36, change "-NM2" to -- -NH$_2$ --.
Lines 38 and 46, change "-N=and" to -- -N= and --.
Line 41, change "-CH3" to -- -CH$_3$ --; delete "-" before -- AR -- and start a new paragraph.
Line 45, delete "-" before -- X -- and start a new paragraph.
Line 51, change "H5" to -- H$_5$ --.
Line 53, change "monosaceharidic" to -- monopolysaccharidic --.
Line 60, change "β" (first occurrence) to -- β- --.
Line 64, change "(1→4)" to -- (1→-4) --.
Line 67, change "(→3)" to -- (1→3) --.

Column 15,
Line 14, change "OCOR" to -- -OCOR --.
Line 28, delete "by" at end of line.

UNITED STATES PATENT AND TRADEMARK OFFICE
CERTIFICATE OF CORRECTION

PATENT NO. : 6,844,328 B2
DATED : January 18, 2005
INVENTOR(S) : Giuliana Miglierini et al.

It is certified that error appears in the above-identified patent and that said Letters Patent is hereby corrected as shown below:

<u>Column 16,</u>
Line 21, insert -- , -- before "p-toluenesulphonylbromide".
Line 22, change "p-toluenesulphonylcloride" to -- p-toluenesulphonylchloride --.

Signed and Sealed this

Tenth Day of May, 2005

JON W. DUDAS
*Director of the United States Patent and Trademark Office*